US008821506B2

(12) United States Patent
Mitchell

(10) Patent No.: US 8,821,506 B2
(45) Date of Patent: Sep. 2, 2014

(54) BONE SCREW

(76) Inventor: Michael David Mitchell, Spartanburg, SC (US)

(*) Notice: Subject to any disclaimer, the term of this patent is extended or adjusted under 35 U.S.C. 154(b) by 983 days.

(21) Appl. No.: 11/736,943

(22) Filed: Apr. 18, 2007

(65) Prior Publication Data

US 2010/0030135 A1 Feb. 4, 2010

Related U.S. Application Data

(60) Provisional application No. 60/799,472, filed on May 11, 2006.

(51) Int. Cl.
*A61B 17/88* (2006.01)
*A61B 17/86* (2006.01)
*A61M 31/00* (2006.01)
*A61B 17/70* (2006.01)

(52) U.S. Cl.
CPC ............ *A61M 31/00* (2013.01); *A61B 17/7037* (2013.01); *A61B 17/864* (2013.01); *A61B 17/7032* (2013.01); *A61B 17/7098* (2013.01)
USPC ................ 606/94; 606/271; 606/308

(58) Field of Classification Search
CPC ........... A61B 17/7094; A61B 17/7097; A61B 17/8816; A61B 17/8841
USPC ...................................... 606/92–94
See application file for complete search history.

(56) References Cited

U.S. PATENT DOCUMENTS

| 3,352,531 A | 11/1967 | Kilmarx |
| 3,409,015 A | 11/1968 | Swanson |
| 3,577,992 A | 5/1971 | Merry et al. |
| 3,625,793 A | 12/1971 | Sheridan et al. |
| 3,726,282 A | 4/1973 | Patel |
| 4,130,617 A | 12/1978 | Wallace |
| 4,274,163 A | 6/1981 | Malcom et al. |
| 4,399,814 A | 8/1983 | Pratt, Jr. et al. |
| 4,653,489 A | 3/1987 | Tronzo |

(Continued)

FOREIGN PATENT DOCUMENTS

| JP | 2003-159258 | * | 6/2003 | ............. A61B 17/58 |
| JP | 2003159258 A | * | 6/2003 | ............. A61B 17/58 |
| WO | WO 2006/070961 A2 | | 7/2006 | |

OTHER PUBLICATIONS

Eisner, W., DePuy Spine Launches Confidence Spinal Cement System (Jun. 2, 2008) DePuy Spine, U.S.A.

(Continued)

*Primary Examiner* — Michael T Schaper
(74) *Attorney, Agent, or Firm* — Thomas A. O'Rourke; Bodner & O'Rourke, LLP

(57) ABSTRACT

A bone screw comprises an interior channel and at least one opening extending from the interior channel to an exterior of the screw shaft. A head is connected to the screw shaft. A fluid delivery probe comprises an interior channel. The fluid delivery probe is locked to the head so that the fluid delivery probe does not separate from the head under extremely high pressures when a fluid is pumped through the fluid delivery probe and into the screw shaft. Also, a leak-free seal is formed between the fluid delivery probe and the screw shaft so that the leak-free seal does not leak under extremely high pressures when a fluid is pumped through the fluid delivery probe and into the screw shaft.

8 Claims, 8 Drawing Sheets

(56) References Cited

U.S. PATENT DOCUMENTS

| | | | |
|---|---|---|---|
| 5,176,680 A * | 1/1993 | Vignaud et al. | 606/302 |
| 5,209,805 A * | 5/1993 | Spraggins | 156/423 |
| 5,474,555 A | 12/1995 | Puno et al. | |
| 5,507,749 A | 4/1996 | Draenert | |
| 5,554,157 A | 9/1996 | Errico et al. | |
| 5,741,265 A | 4/1998 | Chan | |
| 5,788,702 A | 8/1998 | Draenert | |
| 5,871,484 A * | 2/1999 | Spievack et al. | 606/60 |
| 6,017,350 A | 1/2000 | Long | |
| 6,048,343 A * | 4/2000 | Mathis et al. | 606/916 |
| 6,127,597 A | 10/2000 | Beyar et al. | |
| 6,214,012 B1 * | 4/2001 | Karpman et al. | 606/93 |
| 6,217,581 B1 | 4/2001 | Tolson | |
| 6,402,758 B1 | 6/2002 | Tolson | |
| 6,440,133 B1 | 8/2002 | Beale et al. | |
| 6,554,830 B1 | 4/2003 | Chappius | |
| 6,565,572 B2 * | 5/2003 | Chappius | 600/300 |
| 6,668,688 B2 | 12/2003 | Zhao et al. | |
| 6,676,665 B2 | 1/2004 | Foley et al. | |
| 6,755,829 B1 | 6/2004 | Bono et al. | |
| 6,755,835 B2 | 6/2004 | Schultheiss et al. | |
| 6,783,515 B1 | 8/2004 | Miller et al. | |
| 6,899,714 B2 | 5/2005 | Vaughan | |
| 6,984,063 B2 | 1/2006 | Barker et al. | |
| 7,048,743 B2 | 5/2006 | Miller et al. | |
| 7,141,051 B2 | 11/2006 | Janowski et al. | |
| 7,186,255 B2 | 3/2007 | Baynham et al. | |
| 7,250,055 B1 | 7/2007 | Vanderwalle | |
| 7,294,128 B2 | 11/2007 | Alleyne et al. | |
| 7,354,442 B2 | 4/2008 | Sasso et al. | |
| 7,575,572 B2 * | 8/2009 | Sweeney | 604/264 |
| 7,608,062 B2 * | 10/2009 | Sweeney | 604/264 |
| 7,608,097 B2 * | 10/2009 | Kyle | 606/304 |
| 7,717,947 B1 * | 5/2010 | Wilberg et al. | 606/304 |
| 7,824,412 B2 * | 11/2010 | Falahee | 606/92 |
| 8,062,270 B2 * | 11/2011 | Sweeney | 604/264 |
| 8,231,632 B1 * | 7/2012 | Jordan et al. | 606/92 |
| 8,317,799 B2 * | 11/2012 | Schon et al. | 606/92 |
| 8,366,717 B1 * | 2/2013 | Jordan et al. | 606/94 |
| 8,382,808 B2 * | 2/2013 | Wilberg et al. | 606/304 |
| 8,460,305 B2 * | 6/2013 | Jordan et al. | 606/92 |
| 8,475,505 B2 * | 7/2013 | Nebosky et al. | 606/304 |
| 8,480,681 B2 * | 7/2013 | Jordan | 606/94 |
| 8,579,948 B2 * | 11/2013 | Biedermann et al. | 606/301 |
| 2001/0021852 A1 | 9/2001 | Chappius | |
| 2002/0123752 A1 | 9/2002 | Schultheiss et al. | |
| 2003/0000350 A1 | 1/2003 | Zhao et al. | |
| 2003/0083662 A1 * | 5/2003 | Middleton | 606/72 |
| 2004/0015172 A1 | 1/2004 | Biedermann et al. | |
| 2004/0167625 A1 | 8/2004 | Beyar et al. | |
| 2004/0225292 A1 * | 11/2004 | Sasso et al. | 606/73 |
| 2004/0249347 A1 | 12/2004 | Miller et al. | |
| 2004/0260283 A1 * | 12/2004 | Wu et al. | 606/61 |
| 2004/0267265 A1 * | 12/2004 | Kyle | 606/73 |
| 2005/0033303 A1 * | 2/2005 | Chappuis et al. | 606/80 |
| 2005/0055026 A1 | 3/2005 | Biedermann et al. | |
| 2005/0055030 A1 * | 3/2005 | Falahee | 606/92 |
| 2005/0143748 A1 | 6/2005 | Negroni et al. | |
| 2005/0228385 A1 | 10/2005 | Iott et al. | |
| 2006/0036252 A1 | 2/2006 | Baynham et al. | |
| 2006/0079905 A1 | 4/2006 | Beyar et al. | |
| 2006/0264964 A1 * | 11/2006 | Scifert et al. | 606/92 |
| 2006/0266372 A1 | 11/2006 | Miller et al. | |
| 2007/0027230 A1 | 2/2007 | Beyar et al. | |
| 2007/0032567 A1 | 2/2007 | Beyar et al. | |
| 2007/0055235 A1 | 3/2007 | Janowski et al. | |
| 2007/0190490 A1 | 8/2007 | Giorno | |
| 2007/0233146 A1 | 10/2007 | Henniges et al. | |
| 2007/0260250 A1 * | 11/2007 | Wisnewski et al. | 606/73 |
| 2007/0299450 A1 * | 12/2007 | Her et al. | 606/73 |
| 2008/0009792 A1 | 1/2008 | Henniges et al. | |
| 2008/0027434 A1 | 1/2008 | Zucherman et al. | |
| 2008/0091207 A1 | 4/2008 | Truckai et al. | |
| 2008/0154273 A1 | 6/2008 | Shadduck et al. | |
| 2008/0183215 A1 | 7/2008 | Altarac et al. | |
| 2008/0188858 A1 | 8/2008 | Luzzi et al. | |
| 2008/0188895 A1 | 8/2008 | Cragg et al. | |
| 2008/0243130 A1 | 10/2008 | Paris et al. | |
| 2009/0204158 A1 * | 8/2009 | Sweeney | 606/309 |
| 2009/0264895 A1 * | 10/2009 | Gasperut et al. | 606/104 |
| 2010/0004656 A1 * | 1/2010 | Marins Dos Reis, Jr. | 606/93 |
| 2010/0004692 A1 * | 1/2010 | Biedermann et al. | 606/305 |
| 2010/0042167 A1 * | 2/2010 | Nebosky et al. | 606/315 |
| 2010/0042215 A1 * | 2/2010 | Stalcup et al. | 623/16.11 |
| 2010/0114174 A1 * | 5/2010 | Jones et al. | 606/279 |
| 2010/0298887 A1 * | 11/2010 | Jordan et al. | 606/304 |
| 2010/0298889 A1 * | 11/2010 | Wilberg et al. | 606/305 |
| 2011/0245881 A1 * | 10/2011 | Mitchell | 606/304 |
| 2012/0029432 A1 * | 2/2012 | Sweeney | 604/151 |
| 2012/0203287 A1 * | 8/2012 | Arambula et al. | 606/304 |
| 2013/0096634 A1 * | 4/2013 | Suh | 606/304 |
| 2013/0204263 A1 * | 8/2013 | Jones et al. | 606/94 |
| 2013/0245602 A1 * | 9/2013 | Sweeney | 604/506 |

OTHER PUBLICATIONS

Foley, K.T., CD Horizon Sextant Rod Insertion System Surgical Technique, cover plus 30 pages (Jun. 2003) Medtronic Sofamor Danek USA, Inc., U.S.A.

McKoy Be, An Yh, "An injectable cementing screw for fixation in osteoporotic bone", J Biomed Mater Res. 2000;53(3):216-20, Orthopaedic Materials Testing Laboratories, Department of Orthopaedic Surgery, Medical University of South Carolina.

Krebs J, Ferguson SJ, Bohner M, Baroud G, Steffen T, Heini PF, "Clinical measurements of cement injection pressure during vertebroplasty" Spine. Mar. 1, 2005; 30(5): E118-22, M.E. Muller Institute for Surgical Technology and Biomechanics, Bern, Switzerland.

Baroud G, Steffen, T, "A new cannula to ease cement injection during vertebroplasty" Fur Spine J. Jun. 2005; 14(5):474-9. Epub Jan. 26, 2005 Orthopaedic Research Laboratory, Division of Orthopaedic Surgery, Royal Victoria Hospital, McGill University, Montreal, QC, Canada.

DiscOTech, Hi-Visco Flow, http://222.disc-o-tech.com/Articles/_Article._asp.Category, Apr. 14, 2006.

An, Yehuei H., MD, Internal Fixation in Osteoporotic Bone, 2001, Charleston, SC, Chapters 20, 21, 22, 32, 33, 35 and 36.

* cited by examiner

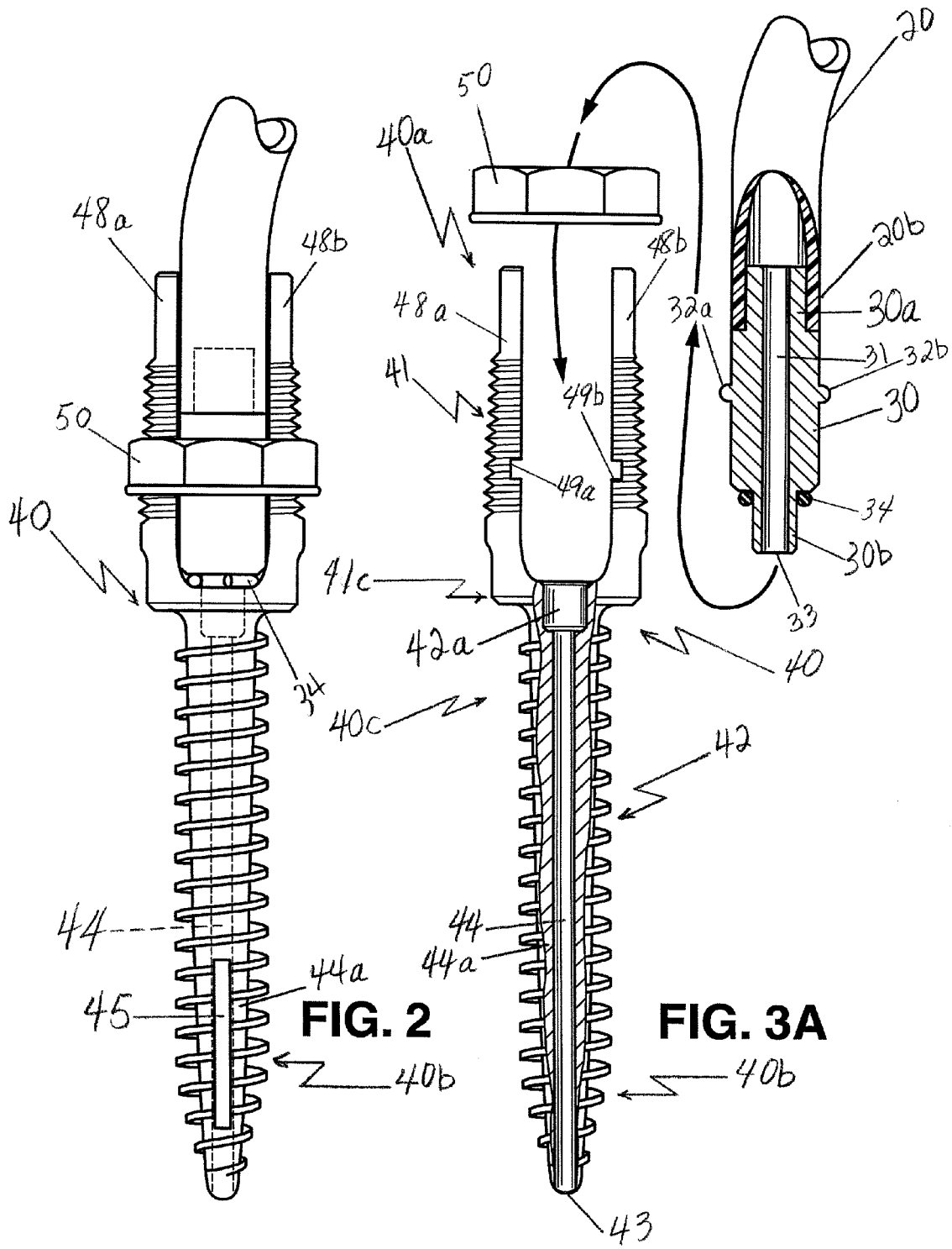

BONE SCREW

CROSS-REFERENCE TO RELATED APPLICATIONS

The present application hereby claims priority to U.S. Provisional Application Ser. No. 60/799,472 filed May 11, 2006.

STATEMENT REGARDING FEDERALLY SPONSORED RESEARCH OR DEVELOPMENT

N/A

BACKGROUND OF THE INVENTION

The present invention pertains to method and apparatus for anchoring bone screws into bones of living beings and injecting under high pressure materials that are high in viscosity.

One technique for inserting and anchoring bone screws relies on use of an expandable device that is inserted into a starter cavity produced by sharp mechanical means, which may include a drill, operating the expandable device to expand the size of the cavity, operating the expandable device to allow the device to contract, withdrawing the device from the expanded cavity, pumping some quick hardening, less viscous cement into the expanded cavity, inserting the desired screw into the cement-filled cavity, and removing the excess cement, if any, that is displaced by the insertion of the screw. This technique has been used in connection with screws that are inserted into the pedicle of the vertebra.

Because of the need to create the cavity to receive the cement, this procedure involves time and expense to create the cavity for the screw and cement. The use of a less viscous cement increases the risk that the cement will extravasate and leak into areas where it would cause harm to the patient.

SUMMARY

A bone screw comprises a shaft, a head, a fluid delivery probe, and a nut. The shaft comprises a proximal end and a distal end. The shaft further comprises a cannula that extends at least partially through the shaft. The cannula comprises an entrance at the proximal shaft end, and an elongated portion that extends from the entrance through the shaft towards the distal shaft end. The circumference of the shaft entrance is greater than the circumference of the elongated portion. The head extends away from the proximal shaft end. The head comprises a plurality of arms and a plurality of detents. Each of the arms comprise an exterior surface comprising exterior threads and an inner surface comprising a detent. The fluid delivery probe comprises a proximal end, a distal end, an intermediate section, and a delivery probe shoulder that connects the intermediate section and the distal end. The circumference of the intermediate section is greater than the circumference of the distal end. The fluid delivery probe further comprises a plurality of protrusions that extend radially from the intermediate section, and a gasket disposed against the delivery probe shoulder, wherein the gasket comprises a circumference at least as large as the cannula entrance circumference. The nut is threaded onto the exterior threads and located at the intermediate section of the fluid delivery probe. The fluid delivery probe is fastened to the head and the distal end of the fluid delivery probe is disposed within the cannula entrance, the protrusions are interlocked with the detents, and the gasket is disposed between the proximal shaft end and the delivery probe shoulder.

BRIEF DESCRIPTION OF THE DRAWINGS

FIG. 2 is a front plan view of components of the embodiment shown in FIG. 1 with dashed lines indicating structure that ordinarily would not be visible in the view shown in FIG. 2 due to the opacity of various structures.

FIG. 3A schematically represents an assembly view of components of the embodiment shown in FIG. 2 but with portions cut away and revealed in cross-section.

DETAILED DESCRIPTION OF THE PREFERRED EMBODIMENTS

Reference now will be made in detail to the presently preferred embodiments of the invention, one or more examples of which are illustrated in the accompanying drawings. Each example is provided by way of explanation of the invention, which is not restricted to the specifics of the examples. In fact, it will be apparent to those skilled in the art that various modifications and variations can be made in the present invention without departing from the scope or spirit of the invention. For instance, features illustrated or described as part of one embodiment, can be used on another embodiment to yield a still further embodiment. Thus, it is intended that the present invention cover such modifications and variations as come within the scope of the appended claims and their equivalents. The same numerals are assigned to the same components throughout the drawings and description.

Figure 1:
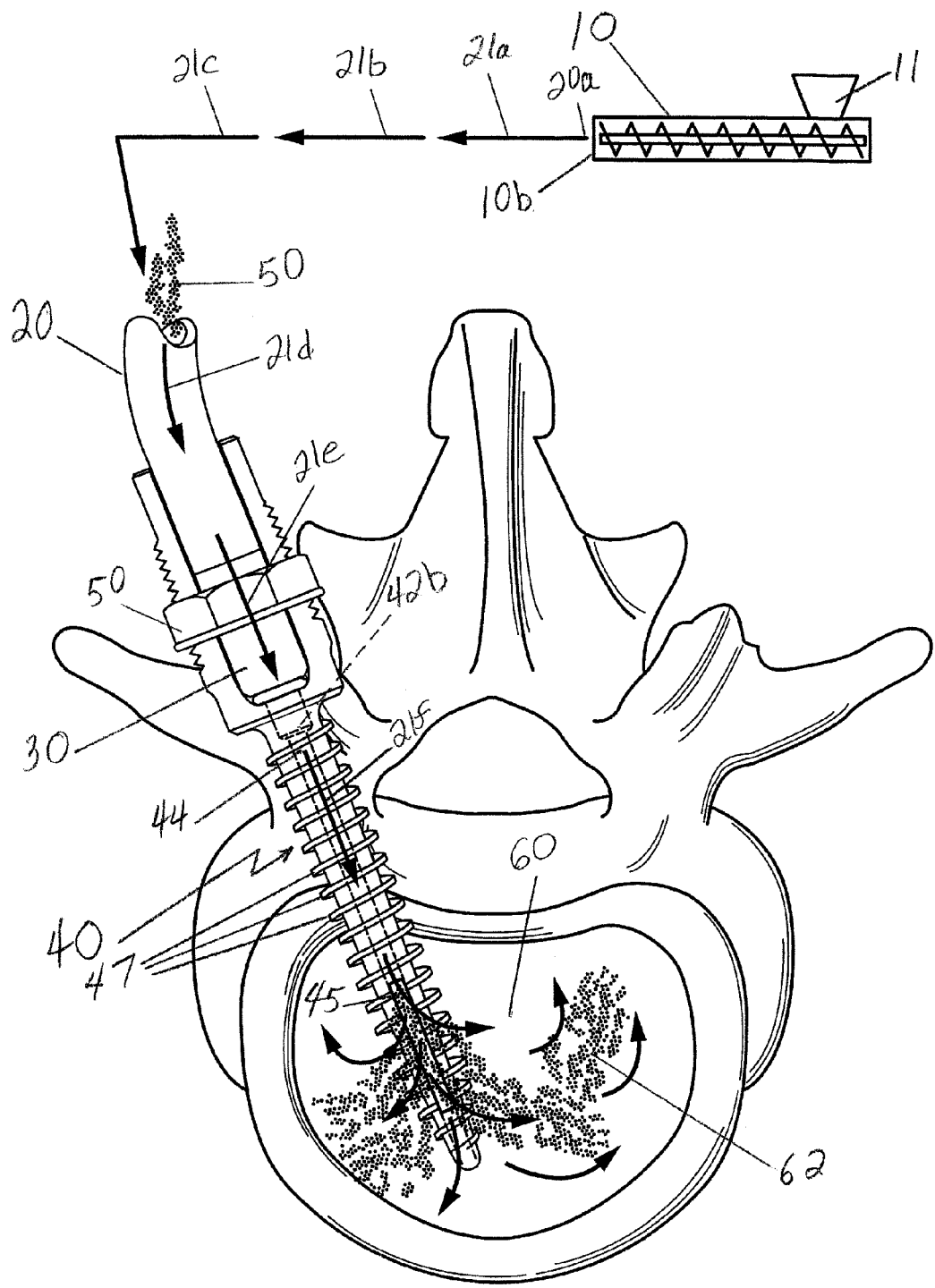
FIG. 1 is an elevated perspective view of an embodiment of the present invention shown in use with elements depicted schematically and with portions of the anatomy removed in order to reveal features of the present invention.

An apparatus for and method of anchoring a bone screw such as a pedicle screw into a vertebral body is shown in relation to FIG. 1. Initially, apparatus and method suitable for use wherein there has been an open incision will be described.

In accordance with an embodiment of the present invention, a fluid insertion device provides cementitious fluid through a hollow feeder tube and thence into a fluid delivery probe that is selectively attachable and detachable to the proximal portion of a cannulated pedicle screw. As shown in FIG. 1, an embodiment of the apparatus of the present invention can include a fluid insertion device that is schematically represented and indicated by the numeral 10. The discharge end 10b of the fluid insertion device 10 is at the distal end 10b thereof and connected to the proximal end 20a of the hollow feeder tube 20. As shown in FIG. 3A, the distal end 20b of the feeder tube 20 is connected to the proximal end 30a of the fluid delivery probe 30. The distal end 30b of the fluid delivery probe 30 is inserted into and connected to the proximal end 42a of the cannula 44 that is defined through the central axis of the shaft 42 of a cannulated pedicle screw 40. The distal end 30b of the delivery probe 30 is selectively detachable and attachable to the proximal end 40a of the cannulated screw 40.

As schematically shown in FIG. 1, the hollow feeder tube 20 has a proximal end 20a that is selectively connectable and disconnectable to the fluid insertion device 10. As shown in FIG. 3A for example, the fluid delivery probe 30 has a proximal end 30a that is connected to the distal end 20b of the feeder tube 20.

Figures 3B, 3C:
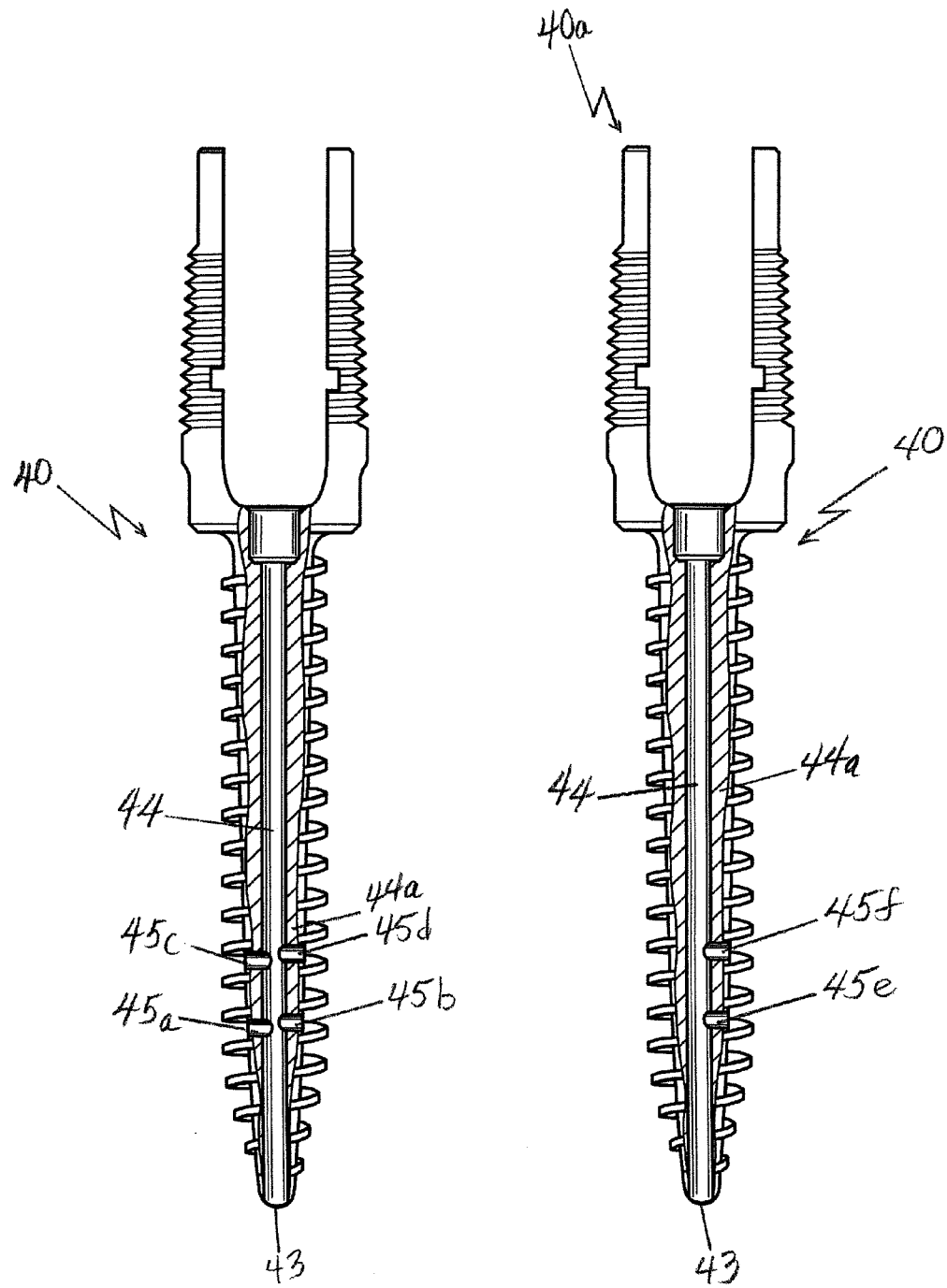
FIG. 3B illustrates an alternative embodiment of a component of the device of the present invention shown partially in cross-section.
FIG. 3C illustrates a further alternative embodiment of a component of the present invention with portions cut away and revealed in cross-section.
Figure 4:
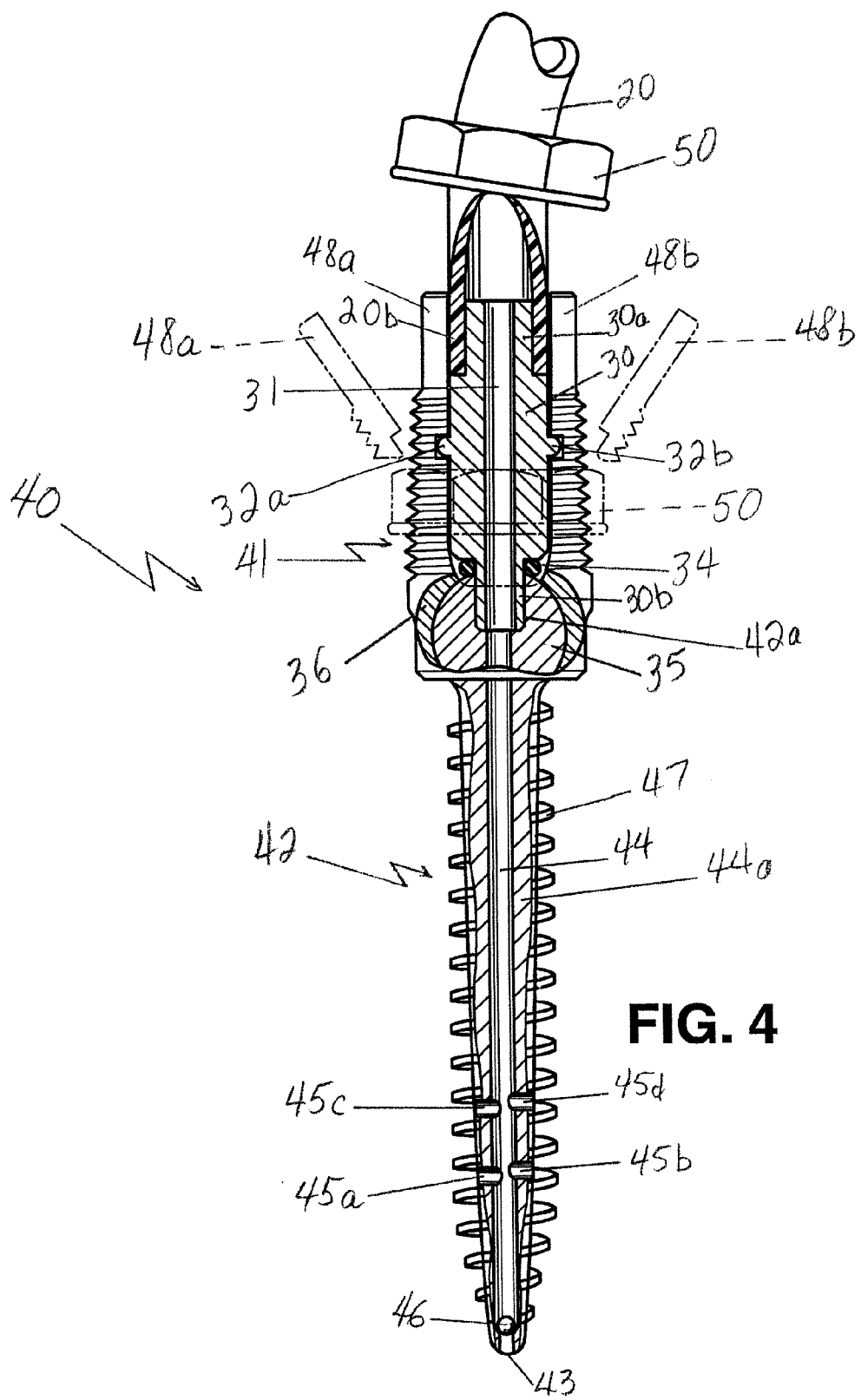
FIG. 4 is a view shown in partially in cross-section of the alternative embodiment in a fully assembled view as it would be configured after insertion into the anatomy and ready for dispensing the filling substance and with elements shown in phantom (chain-dashed lines).
Figure 5:
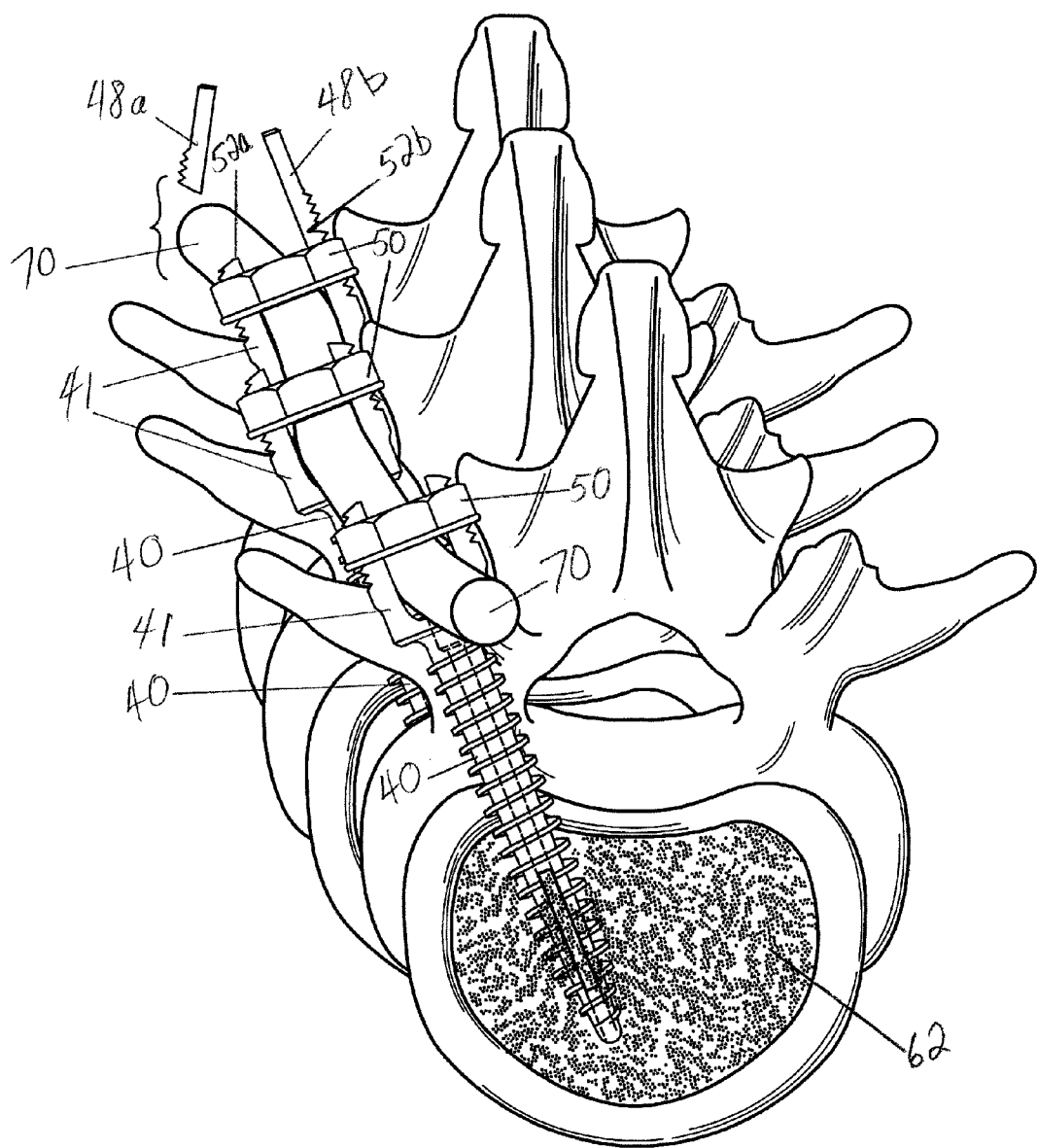
FIG. 5 is an elevated perspective view of an embodiment of the present invention shown in use with portions of the anatomy removed in order to features of the present invention.
Figure 6:
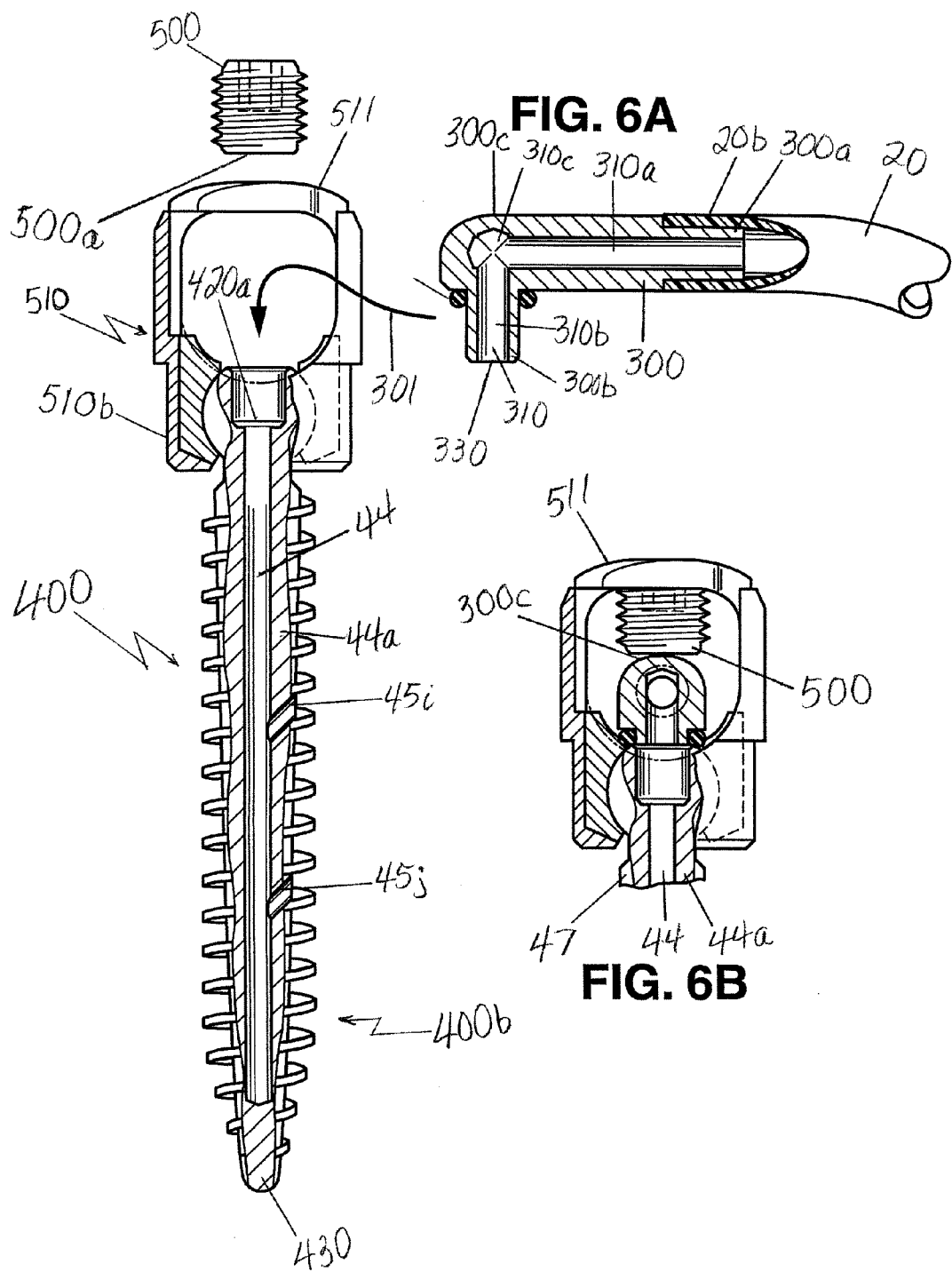
FIG. 6A illustrates additional alternative embodiments of components of the present invention with portions cut away and revealed in cross-section.
FIG. 6B illustrates an assembled view of portions of the components illustrated in FIG. 6A with one of the elements rotated 90° from the view shown in FIG. 6A.

As shown in FIG. 3A, the pedicle screw 40 has a proximal portion 40a with a head 41 at the free end of the proximal portion 40a and an intermediate portion 40c connecting the proximal portion 40a and the distal portion 40b. A tip 43 is provided on the free end of the distal portion 40b of the screw 40. The pedicle screw 40 can have either an uniaxial head (FIGS. 1, 2, 3A, 3B, 3C, 5 and 7) or a polyaxial head (FIGS. 4 and 6). The uniaxial head remains fixed with respect to the central axis of the elongated body of the screw 40. The polyaxial head is configured to be pivotable with respect to the central axis of the elongated body 42 of the screw 40. Some examples of polyaxial heads of pedicle screws are disclosed in U.S. Patent Application Publication No. US2005/0228385A1 and U.S. Pat. Nos. 5,474,555 and 5,554, 157, which are hereby incorporated herein in their entireties by this reference. As shown in FIG. 4, the proximal end of the shaft 42 of the screw 40 defines an arcuately shaped bulb 35 that is configured to be rotatable relative to a cavity defined in a socket 36 formed in the distal end of the head 41 of the screw. The bulb 35 defines a fill cavity 42a at the proximal end of the cannula 44, and the fill cavity 42a is configured to receive therein the distal end 30b of the fluid delivery probe 30.

As shown in FIG. 3A for example, the axially elongated pedicle screw 40 has an interior channel, or cannula 44, extending axially through generally the central axis of the screw 40. The cannula 44 is defined by the interior surface of the sidewall 44a of the screw. As shown in FIG. 2, the cannulated pedicle screw 40 can be is provided with one or more fluid discharge openings 45 through a generally distal portion 40b thereof. At least one fluid discharge opening 45 extends from the cannula 44 (indicated schematically in FIG. 2 by the dashed line) through the sidewall 44a of the screw 40 in the distal portion 40b. No discharge openings 45 are provided through the sidewall 44a of the shaft 42 of the screw for most of the length of the shaft's length, as only the distal portion of the shaft is configured with any discharge openings 45

As shown in FIG. 2 for example, the discharge opening 45 of the screw 40 can be configured as an elongated slot that has its longest dimension extending generally in the axial direction. The elongated slot desirably can be configured as a unidirectional slot that opens only through one section of the sidewall 44a of the screw 40 and thus permits the surgeon to direct the discharge of cementitious fluid in a preferred direction into the vertebral body 60. Alternatively, the slot can be a through slot that extends completely through from one sidewall of the screw 40 to the opposite sidewall of the screw 40. Alternatively, a plane extending through a first slot can be disposed perpendicular to a plane extending through a second slot. Alternatively, one of the slots can be disposed at least in part, closer to the tip 43 of the screw than any portion of the other slot.

Figure 3D:
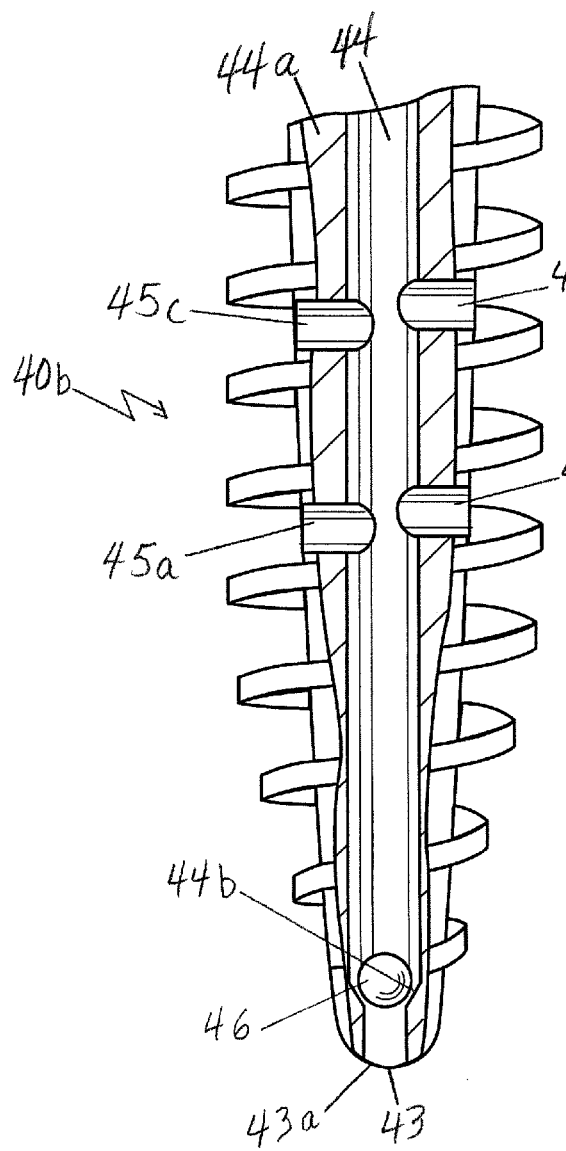
FIG. 3D is a cross-sectional view of a partial section of an alternative embodiment of a component of the present invention.

As shown in a cross-sectional view in each of FIGS. 3B, 3C and 3D for example, the discharge opening of the screw 40 can be configured as a cylindrically-shaped bore that radially extends through the sidewall and into the cannula. As shown in FIGS. 3B, 3C and 3D, more than one such bore can be provided, with the number of bores determining the flow rate from the cannula. As shown in FIGS. 3B and 3D, a first pair of bores 45a, 45b can be disposed with each of the bores 45a, 45b in the first pair disposed on opposite sides of the screw 40 and with each bore's 45a, 45b central axis slightly offset from the other bore's 45a, 45b central axis when viewed relative to the axial direction of the screw 40. Similarly, as shown in FIGS. 3B and 3D, a second pair of bores 45c, 45d can be disposed farther from the tip 43 of the screw 40 than the first pair of bores 45a, 45b. Each of the bores 45c, 45d in the second pair can be disposed on opposite sides of the sidewall 44a of the screw 40 and with each bore's 45c, 45d central axis slightly offset from the other bore's 45c, 45d central axis when viewed relative to the axial direction of the screw 40. However, the central axes of all four of the bores 45a, 45b, 45c, 45d desirably reside in the same plane that includes the central axis of the screw 40.

Alternatively, as shown in FIG. 3C for example, each of a pair of bores 45e, 45f can be disposed on the same side of the sidewall 44a of the screw 40 and with each bore's 45e, 45f central axis residing in the same plane that includes the central axis of the screw 40. This configuration permits the surgeon to direct the discharge of cementitious fluid in a preferred direction into the vertebral body. One of the bores 45f can be disposed closer to the proximal end 40a of the screw 40 than the other bore 40e.

Figure 3E:
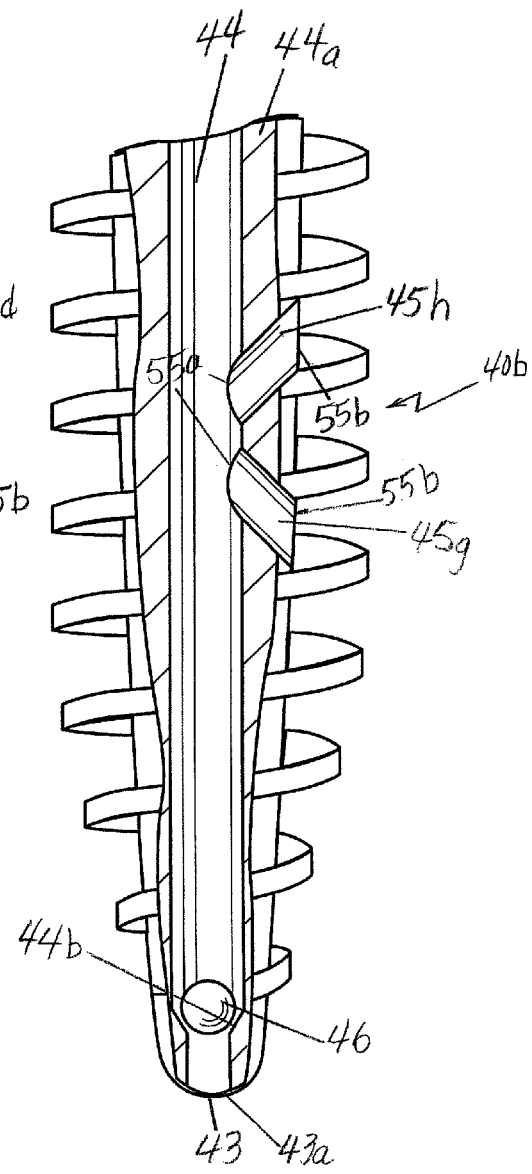
FIG. 3E is a cross-sectional view of a partial section of a further alternative embodiment of a component of the present invention.

Alternatively, as shown in FIGS. 3E and 6A for example, the discharge opening of the screw can be configured as a cylindrically-shaped bore 45g, 45h, 45i, 45j that extends through the sidewall 44a and into the cannula 44 along a central axis that is not normal to the central axis of the cannula 44 and thus is not in a radial direction. As shown in FIGS. 3E and 6A, the bore's 45g, 45h, 45i, 45j axis desirably extends at a 45 degree angle from the central axis of the cannula 44, which thus is at a 45 degree angle from the radius that extends from the central axis of the cannula 44. Other angular orientations can be chosen. Having a variety of angular orientations provides the surgeon with maximum flexibility in accommodating the different anatomies that are likely to be encountered.

As shown in FIGS. 3E and 6A, more than one such bore 45g, 45h, 45i, 45j can be provided, with the number of bores 45g, 45h, 45i, 45j determining the flow rate from the cannula 44. Moreover, each of the bores 45g, 45h, 45i, 45j can be disposed on the same side of the sidewall 44a of the screw 40 and with each bore's 45g, 45h, 45i, 45j central axis residing in the same plane that includes the central axis of the screw 40. This configuration permits the surgeon to direct the discharge in a preferred direction into the vertebral body. As shown in FIG. 3E, each bore 45g, 45h has an entrance orifice 55a through the interior surface of the sidewall 44a that defines the cannula 44. Each bore 45g, 45h has an exit orifice 55b defined through the exterior surface of the sidewall 44a that defines the cannula 44 of the screw. The exit orifices 55b of the bores 45i, 45j can both be closer to the proximal end of the screw 40 than the entrance orifices 55a formed in the sidewall 44a of the screw 40. One of the bores 45g can be disposed closer to the tip 43 of the screw 40 than the other bore 45h.

Moreover, it is believed that when the cementitious fluid hardens, the direction in which the fluid enters the vertebral body will result in greater integrity of the hardened fluid in that same direction. Thus, it is desirable to direct at least one bore in the direction of the bore 45h shown in FIG. 3E that points back toward the proximal end of the screw 40. In this way, the fluid directed from this bore 45h will act in the same manner as a fish hook barb and retard any tendency for the screw to move out of the vertebral body. Accordingly, as shown in FIG. 6A, an additional embodiment of the screw 400 desirably has more than one such bore 45i, 45h.

To aid the surgeon in positioning the discharge opening 45, whether slot(s) or bore(s), whether radially through the sidewall 44a or at an angle through the sidewall 44a, the proximal end of the screw can be provided with one or more markers that indicate where and how the discharge opening(s) is/are oriented so that whether the surgery is done percutaneously or open, the desired position of the discharge opening(s) could be observed prior to introducing the cementitious material.

As shown in FIGS. 3D and 3E, in embodiments of the screw having a cannula 44 that extends completely through the tip 43 of the screw 40, it may be desirable to block off the opening 43a of the cannula 44 in the tip 43 of the screw. In such cases, a plug such as a solid steel ball 46 can be introduced into the cannula 44 and rest on a shoulder portion 44b within the cannula 44 to thereby block off the opening 43a in the tip 43 of the screw 40. This opening 43a in the tip 43 of the screw is desirably of a smaller diameter than the diameter of the cannula 44 in the remaining portion of the shaft of the screw.

In accordance with an embodiment of the method of the present invention, the distal portion of the screw can be introduced through the pedicle of a vertebra and into the vertebral body of the vertebra. This can be done in a conventional way such as using an awl and/or a punch to start a hole through the pedicle and then rotating the screw about its longitudinal axis with a suitable implement that results in the advancement of the screw into the pedicle due to the pitch of the threads formed in the exterior surface of the wall that forms the shaft of the screw. Desirably, as shown in FIG. 1, the exterior surface of the wall of the shaft of the screw is provided with threads 47 that are configured with suitable pitch that is designed to render the screw self-tapping upon rotation of the screw.

In accordance with an embodiment of the method of the present invention, a fluoroscope desirably can be used to observe the advancement of the screw into the vertebral body 60. When the fluid discharge opening 45 in the screw 40 is oriented so as to direct fluid flowing out of the discharge opening 45 in a desired direction into the vertebral body of the vertebra, then the advancement of the screw 40 can be stopped. The particular embodiment of the screw 40 will be chosen according to the particular vertebra in which the screw 40 is to be placed.

In accordance with an embodiment of the method of the present invention, a fluid delivery probe can be provided and connected to a filler tube that is connected to a fluid insertion device. As shown in FIG. 3A for example, a fluid delivery probe 30 has a proximal end 30a connected to the distal end 20b of the filler tube 20. As schematically shown by the arrows 21a, 21b, 21c in FIG. 1, the proximal end 20a of the filler tube 20 is connected to the fluid insertion device 10. In the embodiment shown in FIG. 3A, the fluid delivery probe 30 extends axially in generally the same direction as the filler tube 20 and thus is generally "in-line" with the axis of the filler tube 20.

In the embodiment of FIGS. 6A and 6B, the head of the screw 400 is capped so as to preclude direct axial access to the cannula 44 through the head. Thus, access to the cannula 44 by the fluid delivery probe 300 must be directed from the side of the head as shown schematically by the arrow 301 in FIG. 6A. In the embodiment shown in FIGS. 6A and 6B, the proximal end 300a of the fluid delivery probe 300 extends axially with the distal end 20b of the filler tube 20. However, the distal end 300b of the fluid deliver probe 300 extends axially generally at a right angle to the axial direction of the filler tube 20 and thus is generally "out-of-line" with the axis of the filler tube 20. The embodiment shown in FIGS. 6A and 6B is thus adapted for use in connection with a screw head that is not threaded on the exterior to receive a nut 50 such as shown in FIG. 3A.

As shown in FIGS. 3A and 6A, each fluid delivery probe 30, 300 defines therein a hollow channel 31, 310 that is disposed generally along the central axis of the fluid delivery probe. In the embodiment shown in FIG. 6A, the channel 310 forms two legs 310a, 310b joined by a right angle elbow 310c. The diameter of the channel 310 desirably is larger than the diameter of the cannula 44 in the shaft of the screw 400, but desirably is at least as large as the diameter of the cannula 44, which desirably is formed as a through bore at least as large as would be found in a 10/11 gauge injection needle (1.69 mm/0.0665 inches). However, in some embodiments, the diameter of the bore in the cannula can be as small as would be found in a 14 gauge needle (1.628 mm/0.0641 inches) or a 15 gauge needle (1.450 mm/0.0571 inches).

In the embodiment show in FIGS. 2 and 3A, each of a pair of protrusions, or opposed ribs 32a, 32b extend radially from the exterior surface of the fluid delivery probe 30. The proximal end 40a of the head 41 of the screw 40 includes two opposed arms 48a, 48b that extend axially and have threaded exterior surfaces. The surfaces of the arms 48a, 48b that face one another are the interior surfaces, and each interior surface of each arm defines a recess 49a, 49b that is configured to receive therein one of the ribs 32a, 32b that is defined on the exterior surface of the fluid delivery probe 30.

In accordance with an embodiment of the method of the present invention, the fluid insertion device 10 can be operated so as to fill the filler tube 20 and fluid delivery probe 30 with fluid so that all air is purged from the filler tube 20 and the fluid delivery probe 30. As schematically shown in FIG. 1 for example, the fluid insertion device 10 can be operated to deliver cementitious fluid 62 to the filler tube and thence to the channel (not indicated in FIG. 1) of the fluid delivery probe 30. As schematically shown in FIGS. 3A and 6A for example, the outlets 33, 330 of the fluid delivery probes 30, 300, respectively, are disposed to expel into the environment, cementitious fluid and any air that exists in the filler tube 20 and fluid delivery probe 30, 300.

In further accordance with an embodiment of the method of the present invention, the fluid delivery probe can be connected to the head of the screw so as to form a high pressure seal between the fluid delivery probe and the head of the screw.

As shown in FIGS. 3A and 6A, a sealing O-ring gasket 34, 340 is disposed against a shoulder connecting an intermediate section of the fluid delivery probe 30, 300 and the distal end 30b, 300b of the fluid delivery probe. The intermediate section is situated between the proximal end 30a, 300a and the distal end 30b, 300b of the fluid delivery probe. As schematically shown in FIGS. 2 and 3A, once the distal end 30b of the fluid delivery probe 30 is inserted into the distal end 41c of the head 41 of the screw, the O-ring 34, which is shown partially cut away in FIG. 2, is disposed against the delivery probe shoulder and the proximal end of the shaft 42 at the cannula entrance 42a.

As shown in FIGS. 2, 3A, 6A and 6B, the cannula entrance 42a at the proximal end of the shaft 40 is shaped to accept the distal end 30b of the fluid delivery probe 30. For example, as shown in the figures, the cylindrical distal end 30b of the fluid delivery probe 30 is disposed within the cylindrical cannula entrance 42a. Thus, in this example, the circumferences, which are defined by the diameters of the distal end 30b of the fluid delivery probe 30 and the cannula entrance 42a, are approximately equal so that the distal end 30b can be inserted into the cannula entrance 42a, the cannula entrance 42a being only slightly larger than the fluid deliver probe's distal end 30b. And, the gasket 34 which is disposed between the delivery probe shoulder in FIG. 3A and between the proximal shaft end at the cannula entrance 42a has a corresponding circumference at least as large as the cannula entrance 42a circumference. Further, as can now be appreciated, the intermediate section of the fluid delivery probe 30 has a circumference greater than the circumference of the distal end 30b of the fluid delivery probe 30 thereby forming the delivery probe shoulder that connects the intermediate section to the distal end 30b. Additionally, the proximal end 30a of the fluid delivery probe 30 has a circumference that is less than the circumference of the intermediate section of the fluid delivery probe 30.

In the embodiment shown in FIGS. 2 and 3A, a nut 50 is threaded onto the threaded exterior surface of the proximal end 40a of the head 41 of the screw 40. As the nut 50 is advanced in the direction toward the distal end 40b of the screw 40, then the plurality of arms 48a, 48b of the head 41 of the screw 40 are compressed or pressed toward one another thereby locking the ribs 32a, 32b that extend radially from the exterior surface of the fluid delivery probe 30 into the detents 49a, 49b in the arms 48a, 48b of the head 41. The nut 50 is advanced so it is located at an intermediate section of the fluid delivery probed situated between the proximal end 30a and the distal end 30b of the fluid delivery probe 30 (for example, as illustrated in FIGS. 1, 4, and 5).

The detents 49a, 49b and ribs 32a, 32b are disposed so that when the ribs 32a, 32b are locked into the detents 49a, 49b, then the distal end 30b of the fluid delivery probe 30 and the distal end 41c of the head 41 of the screw 40 are sealed together via the O-ring 34 so that the cementitious fluid flows from the outlet 33 of the channel 31 of the fluid delivery probe 30 into the entrance 42a of the cannula 44 in the screw 40 rather than escaping out of the head 41 of the screw 40 and into the environment surrounding the head 41 of the screw 40. This arrangement ensures against escape of the cementitious fluid where the fluid delivery probe 30 is connected to the head 41 of the screw 40 and the outlet 33 of the channel 31 of the fluid delivery probe 30 is joined to the entrance 42a of the cannula 44 in the screw 40.

So, as shown in FIG. 2 with reference to FIG. 3A, the fluid delivery probe 30 is fastened to the head 41, the distal end 30b of the fluid delivery probe 30 is disposed within the cannula entrance 42a, each protrusion 32a and 32b is interlocked with each detent 49a and 49b, and the gasket is disposed between the proximal end of the shaft 42 near the cannula entrance 42a and the delivery probe shoulder located where the distal end 30 and intermediate section of the fluid delivery probe 30 connect.

Alternatively, in the embodiment shown in FIGS. 6A and 6B, a nut 500 having threads on its exterior surface, is threaded through an axially extending, threaded opening formed in the cap 511 of the head 510 of the screw 400. As the nut 500 is advanced in the direction toward the distal end 400b of the screw 400, then the forward end 500a of the nut 500 is pressed against the back 300c of the elbow of the fluid delivery probe 300 thereby locking the fluid delivery probe 300 against movement in the axial direction away from the distal end 400b of the screw 400. The externally threaded nut 500 and the cap are desirably configured and disposed so that when the forward end 500a of the nut 500 is contacting the back 300c of the elbow of the fluid delivery probe 300, then the distal end 300b of the fluid delivery probe 300 and the distal end 510b of the head 510 of the screw 400 are sealed together via the O-ring 340 so that the cementitious fluid flows from the outlet 330 of the channel 310 of the fluid delivery probe 300 into the entrance 420a of the cannula 44 in the screw 400 rather than escaping out of the head 510 of the screw 400 and into the environment surrounding the head 510 of the screw 400. This arrangement ensures against escape of the cementitious fluid where the fluid delivery probe 300 is connected to the head 510 of the screw 400 and the outlet 330 of the channel 310 of the fluid delivery probe 300 is joined to the entrance 420a of the cannula 44 in the screw 400.

The fluid insertion device 10 can be provided by a screw extruder mechanism that is capable of generating pressures within the screw as high as 4,000 pounds per square inch. However, somewhat lower pressures generated in the screw of the present invention can be used, depending upon the viscosity of the flowable fluid that is being used and the configuration of the fluid discharge openings 45 in the distal portion of the pedicle screw. An example of a suitable fluid insertion device is described in U.S. Pat. No. 6,783,515, which is hereby incorporated herein in its entirety by this reference, and another example of a suitable fluid insertion device is available from Discotech Medical Technologies Ltd., of Herzeliya, Israel. The fluid insertion device desirably can be provided with a reservoir full of a flowable, cementitious fluid that is capable of setting to a hardened condition.

In accordance with an embodiment of the present invention, the cementitious fluid 62 can be chosen so that it does not begin setting up until about at least ten minutes after it is introduced into the vertebral body. Cementitious fluid 62 suitable for this purpose includes high viscosity, acrylic cement such as polymethyl methacrylate (PMMA) that is paste-like in consistency yet can be introduced through the bore that is defined by the cannula 44. The chosen fluid 62 desirably has a consistency and viscosity that resembles the viscosity of a clay or PlayDoh brand molding material. Whether this flowable fluid includes calcium phosphate or ceramics or an highly viscous bone cement, it will be characterized by a high viscosity that resists travel from the anchoring site for the screw and further dispersion throughout the body of the patient. Cementitious fluid 62 suitable for this purpose is available under the trade name Hi-Visco Flow and can be obtained from Discotech Medical Technologies Ltd. of Herzeliya, Israel.

In further accordance with an embodiment of the method of the present invention, the fluid insertion device can be operated to discharge fluid from the discharge channel of the screw and into the vertebral body. As schematically shown by the arrows 21a, 21b, 21c in FIG. 1 for example, the fluid insertion device 10 can be operated to pump under pressure, cementitious fluid 62 from a reservoir 11 and through the filler tube 20. As schematically indicated by the arrow 21e, the fluid is pumped into and out of the outlet of the channel of the fluid delivery probe 30. Upon leaving the channel of the fluid delivery probe 30, the cementitious fluid travels under pressure through the entrance 42b of the cannula and through the length of the cannula 44 as indicated by the arrow 21f. Upon reaching the discharge opening 45 that is defined in the distal portion of the screw 40, the fluid 62 exits the screw 40 and enters the vertebral body 60 as schematically indicated by the curved arrows. During operation of the fluid insertion device 10, the surgeon can monitor the discharge of the cementitious fluid 62 into the vertebral body 60 by use of a fluoroscope or other means of visual observation.

In accordance with an embodiment of the present invention, once the cementitious fluid 62 fills the vertebral body 60 to the surgeon's desired extent, then the surgeon or other personnel discontinues operation of the fluid insertion device 10, and thereafter the fluid delivery probe 30 is detached from the screw 40. The detachment of the fluid delivery probe 30 can proceed in reverse order of the manner of attachment described above. A cap can be inserted into the fill cavity 42a and sealed therein by the cementitious fluid, and excess fluid removed.

In accordance with an embodiment of the present invention, once the fluid delivery probe has been detached from the screw, support rods then can be attached to the screw, either with or without there having been a cap inserted into the fill cavity 42a. As shown in FIG. 5 for example, each of a plurality of screws 40 is connected to a steel rod 70 and thus is connected to each other. The steel rod 70 is held in place against the head 41 of each screw 40 by a respective nut 50. As schematically shown in FIG. 5, the proximal ends of the arms 48a, 48b of the head 41 of each screw 40 desirably can be broken off along a line of weakness 52a, 52b that is defined transversely across each of the arms 48a, 48b.

Moreover, the invention contemplates both percutaneous and non-percutaneous, i.e., open, embodiments of the apparatus and method. The percutaneous embodiment now will be described with reference to FIG. 7.

Figure 7:
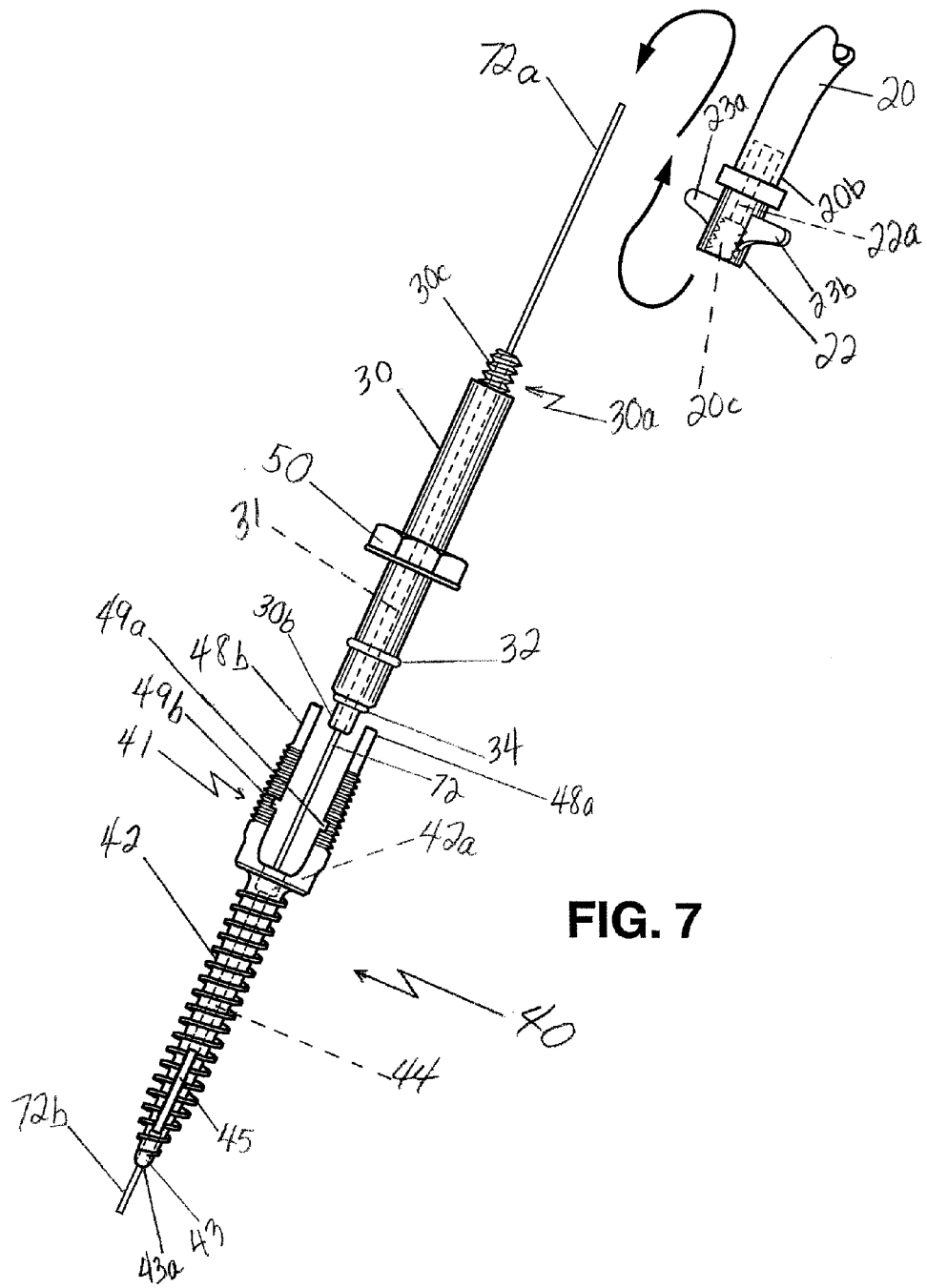
FIG. 7 is an elevated assembly, front plan view with dashed lines indicating structure that ordinarily would not be visible in the view shown in FIG. 7 due to the opacity of various structures.

According to a percutaneous embodiment of the method of present invention, an incision permits insertion of a metal probe, and a hole is made through the pedicle of a vertebra in which it is desired to insert a screw 40. The proximal end 72a of a thin guide wire 72 such as shown in FIG. 7 can be held by the surgeon and the distal end 72b is threaded through the incision and into the hole in the pedicle. A cannulated pedicle screw 40 that is configured according to a percutaneous embodiment of the present invention can be guided by the surgeon into the hole via the guide wire 72 by threading the guide wire 72 through the cannula 44 that is formed axially through the screw 40. Once the tip 43 of the screw 40 is seated in the hole in the pedicle, the head 41 of the screw 40 will protrude through the incision and reside outside the patient's body. The guide wire 72 then can be removed.

A conventional tool can be used to rotate the screw 40, which desirably is self-tapping, into the pedicle while a fluoroscope or similar device can be used to determine when the screw 40 has passed through the pedicle and is desirably located in the vertebral body 60 as shown in FIG. 1. If end opening 43a at the tip 43 of the cannula 44 in the screw 40 should be sealed before introducing the cementitious fluid 62, then a sealing ball 46 is introduced into the cannula 44 of the screw 44 to seal the end opening 43a in the tip 43 of the screw 40.

The proximal end of the feeder tube 20 is connected to the fluid insertion device such as a cement pump. If the screw 40 has a threaded head as shown in FIG. 7, then the mating nut 50 is placed around the fluid delivery probe 30. The distal end 20b of the feeder tube 20 is connected to a connector 22 that has a body that defines a hollow conduit 22a that extends axially through the connector 22. The distal end of the body of the connector 22 can further define a threaded bore 20c that is configured to be threaded to a threaded projection 30c that can be formed at the proximal end 30a of the fluid delivery probe 30. The connector 22 desirably has a pair of opposed wings 23a, 23b radially extending from the body of the connector 22 and configured to facilitate manually connecting the filler tube 20 to the fluid delivery probe 30. The cement pump then can be operated to fill the feeder tube 20 with the cementitious fluid 62 until the fluid forces all of the air out the filler tube 20 and out of the fluid delivery probe 30 that is mounted to the distal end 20b of the filler tube 20.

The distal end 30b of the fluid delivery probe 30 carries an O-ring 34 and becomes seated in the fill cavity 42a in the head of the screw 40. The connector 22 of the feeder tube 20 can be manipulated via a pair of opposed wings 23 thereon until the O-ring 34 is compressed and the fluid delivery probe 30 is snugly seated into the fill cavity 42a in the head 41 of the screw 40. If the screw 40 has a threaded head 41 as shown in FIG. 7, then the mating nut 50 is threaded over the arms 48a, 48b of the proximal end of the screw 40. As the nut 50 is advanced, the recesses 49a, 49b in the arms 48a, 48b close in around the annular rib 32 formed in the distal end of the fluid delivery probe 30 and hold the fluid delivery probe 30 snugly in the fill cavity 42a in the head 41 of the screw 40 to effect a pressure tight seal between the fluid delivery probe 30 and the fill cavity 42a in the head of the screw 40.

Before operating the fluid insertion device to insert the cementitious fluid 62 into the vertebral body 60, the surgeon views the real time x-ray of the position of the distal end of the screw relative to the vertebral body to determine whether the fluid discharge opening 45 in the distal end of the screw 40 is desirably positioned for discharging the cementitious fluid 62.

The various components such as the screws 40, 400, nuts 50, 500, rods 70, caps 511 and screw heads 510 desirably can be made of structurally hard materials such as metals like stainless steel or titanium or ceramic or hard plastics such as PolyEtherEtherKetone (aka PEEK), provided the materials can be given or inherently have, radiographic markers.

While at least one presently preferred embodiment of the invention has been described using specific terms, such description is for illustrative purposes only, and it is to be understood that changes and variations may be made without departing from the spirit or scope of the following claims. For example, the cementitious material enables the screws to be inserted directly into the vertebral body without going through the pedicle. Such a method would allow for anterior or lateral placement of the screws on the vertebral body and be anchored by the injected material.

What is claimed is:

1. An apparatus for delivering highly viscous cementitious fluid into a pedicle and for anchoring a steel rod to the pedicle, said apparatus comprising:
   a probe, said probe comprising a cylinder having a first end and a second end, said first end of said cylinder comprising a cylindrical protrusion extending away from said first end, to form a shoulder thereat; said cylindrical protrusion having a diameter being smaller than a diameter of said cylinder, said cylinder comprising a pair of ribs protruding laterally from opposite sides of its outer surface, said probe comprising a channel extending through said cylinder and said cylindrical protrusion; said second end of said cylinder configured to be fixedly coupled to a feeder tube;

a nut comprising internal threads;
an O-ring seal configured to be received over said cylindrical protrusion of said probe;
a screw, said screw comprising:
   a shaft, said shaft having a first end and a second end, said shaft comprising:
      a cannula configured to begin at said first end of said shaft and to extend along an axis of said shaft at least part way to said second end;
      a plurality of external threads formed on an exterior surface of said shaft;
      a selectively shaped discharge opening in said threaded shaft, configured to extend outward from said cannula, and to be at a selective angle relative to the axis of said shaft;
   a head, said head comprising:
      a cylindrical member having a first end fixedly connected to said first end of said shaft, and extending therefrom along the axis of said shaft to terminate at a second end;
      an opening in said cylindrical member transverse to the shaft axis, said opening beginning at said second end of said cylindrical member and extending part way to said first end of said cylindrical member to form two opposed arms, and to form a shoulder configured to support said O-ring seal;
      a bore beginning at said shoulder of said head of said screw, and extending to interconnect with said cannula of said shaft, said bore configured to seat a portion of said cylindrical protrusion of said probe therein, with said O-ring seal seated between, and sealed against, said shoulder of said head of said screw, and said shoulder of said probe;
      a recess comprising a rectangular cross-section, being respectively formed on each of said two opposed arms, each said recess beginning at said transverse opening and extending away from the axis of said shaft, said recesses of said arms configured to respectively receive said pair of ribs of said probe;
      a plurality of external threads formed over at least a portion of an exterior surface of said cylindrical member, said recess in each of said two opposed arms formed in axial proximity to said portion of the exterior surface with said plurality of threads of said cylindrical member, said plurality of threads on said cylindrical member configured to receive said internally threaded nut to temporarily secure said probe thereto, for use in delivering the highly viscous cementitious fluid through said channel of said probe, through said cannula of said screw, and out said discharge opening;
   wherein said plurality of external threads of said cylindrical member are configured to subsequently receive said nut, for use in securing the rod against said shoulder of said head; and
   wherein said respectively formed recesses in said two opposed arms are configured to create a weakness transverse to each said arm to permit deflection of said arm to break off a portion of each said two opposed arms being proximate to said second end of said cylindrical member.

2. The apparatus according to claim 1 further comprising one or more markers disposed on said head and configured to indicate an orientation of said discharge opening.

3. The apparatus according to claim 1 wherein said external threads are configured to be self-tapping.

4. The apparatus according to claim 1 wherein an outer diameter of said exterior surface of said shaft is tapered between said first and second ends of said shaft.

5. The apparatus according to claim 1 wherein said selectively shaped opening comprises an elongated slot configured with its longest dimension extending substantially parallel to the axis of said shaft.

6. The apparatus according to claim 1 wherein said selectively shaped opening comprises a cylindrical bore that extends radially outward from said cannula.

7. The apparatus according to claim 1 wherein said cannula extends to said second end of said shaft to form an opening thereat; and with said apparatus further comprising a plug disposed within said cannula at said second end of said shaft.

8. The apparatus according to claim 7 wherein said plug comprises a metal ball.

* * * * *